United States Patent
Jung

(10) Patent No.: US 10,292,903 B2
(45) Date of Patent: May 21, 2019

(54) DEVICE FOR CURING OBESITY USING COOLING

(71) Applicant: CLASSYS INC., Seoul (KR)

(72) Inventor: Sung Jae Jung, Seoul (KR)

(73) Assignee: CLASSYS INC., Seoul (KR)

( * ) Notice: Subject to any disclaimer, the term of this patent is extended or adjusted under 35 U.S.C. 154(b) by 625 days.

(21) Appl. No.: 14/910,465

(22) PCT Filed: Aug. 16, 2013

(86) PCT No.: PCT/KR2013/007384
§ 371 (c)(1),
(2) Date: Feb. 5, 2016

(87) PCT Pub. No.: WO2015/020254
PCT Pub. Date: Feb. 12, 2015

(65) Prior Publication Data
US 2016/0175193 A1 Jun. 23, 2016

(30) Foreign Application Priority Data

Aug. 8, 2013 (KR) ........................ 10-2013-0094297

(51) Int. Cl.
*A61F 7/00* (2006.01)
*A61F 7/02* (2006.01)
(Continued)

(52) U.S. Cl.
CPC ............. *A61H 39/06* (2013.01); *A61B 18/02* (2013.01); *A61F 7/007* (2013.01);
(Continued)

(58) Field of Classification Search
CPC combination set(s) only.
See application file for complete search history.

(56) References Cited

U.S. PATENT DOCUMENTS

2003/0097163 A1* 5/2003 Kane .................... A61F 7/02
607/108
2006/0036300 A1* 2/2006 Kreindel ................ A61B 18/14
607/99
(Continued)

FOREIGN PATENT DOCUMENTS

EP         2 241 295 B1    10/2010
KR    10-2008-0049052 A     6/2008
(Continued)

OTHER PUBLICATIONS

Office Action dated Nov. 8, 2016, issued in counterpart Australian Patent Application No. 2013397323. (3 pages).
(Continued)

*Primary Examiner* — Joseph A Stoklosa
*Assistant Examiner* — Adam J Avigan
(74) *Attorney, Agent, or Firm* — Westerman, Hattori, Daniels & Adrian, LLP

(57) ABSTRACT

The present invention relates to a device for treating obesity using cooling, the device comprising: a controller body for setting a cooling temperature and operating time, supplying cooling water for cooling a thermoelectric element, and providing suction force through a vacuum pump; a handpiece body for displaying operating conditions and providing suction force through a suction hole; a cable for connecting the controller body and the handpiece body; a suction cup mounted on the handpiece body to form a suction space; and cooling devices positioned on opposite sides of the suction cup to cool a part to be treated, which has been sucked into the suction space. Further, metallic cooling plates in-molded in a suction cup made of silicone make contact with the part to be treated via a thin silicone layer such that fat can be destroyed efficiently using a small amount of anti-freezing agent while protecting the skin.

9 Claims, 9 Drawing Sheets

(51) Int. Cl.
*A61B 18/00* (2006.01)
*A61B 18/02* (2006.01)
*A61B 90/00* (2016.01)
*A61H 39/06* (2006.01)

(52) U.S. Cl.
CPC ............ *A61B 2018/00291* (2013.01); *A61B 2018/00464* (2013.01); *A61B 2018/00702* (2013.01); *A61B 2018/00791* (2013.01); *A61B 2018/025* (2013.01); *A61B 2090/0463* (2016.02); *A61F 2007/0075* (2013.01); *A61F 2007/0096* (2013.01); *A61F 2007/029* (2013.01); *A61H 2201/0214* (2013.01); *A61H 2201/0242* (2013.01); *A61H 2201/0285* (2013.01); *A61H 2201/165* (2013.01); *A61H 2201/5082* (2013.01); *A61H 2205/083* (2013.01)

(56) References Cited

U.S. PATENT DOCUMENTS

| | | | | |
|---|---|---|---|---|
| 2007/0255362 | A1* | 11/2007 | Levinson | A61F 7/10 607/96 |
| 2008/0287839 | A1 | 11/2008 | Rosen et al. | |
| 2009/0221938 | A1 | 9/2009 | Rosenberg et al. | |
| 2010/0023098 | A1* | 1/2010 | Li | A61F 7/007 607/98 |
| 2010/0280582 | A1* | 11/2010 | Baker | A61F 7/007 607/113 |

FOREIGN PATENT DOCUMENTS

| | | |
|---|---|---|
| KR | 10-2011-0019446 A | 2/2011 |
| KR | 10-2012-0059078 A | 6/2012 |
| KR | 10-2013-0063614 A | 6/2013 |
| WO | 2012/138056 A1 | 10/2012 |

OTHER PUBLICATIONS

Extended (Supplementary) European Search Report (EESR) dated Aug. 25, 2016, issued in counterpart European Patent Application No. 13 89 1027.8. (8 pages).

International Search Report dated May 1, 2014, issued in counterpart application No. PCT/KR2013/007384 (3 pages).

* cited by examiner

DEVICE FOR CURING OBESITY USING COOLING

TECHNICAL FIELD

The present invention relates generally to a device for treating obesity using cooling. More particularly, the present invention relates to a device for treating obesity using low-cost cooling, the device being capable of treating obesity by spreading an anti-freezing agent to a part to be treated without use of an absorption pad or a coupling device, but by surrounding the part with a film to protect a skin, and cooling only a fat portion.

BACKGROUND ART

As well known to those skilled in the art, obesity is caused mainly by the accumulation of neutral fat in such a way that fatty acid and glucose introduced from blood plasma to fat cells are esterified when excessive nutrients are consumed compared to the amount of energy consumption over a long period. Further, when a body mass index (a value obtained by dividing weight in kilograms by height in meters squared) is the reference value (25) or more, it is viewed as being at the level of obesity.

Since it is known that obesity is the source of many illnesses, various dieting methods in various shapes have captured the attention of society. However, in case of severe obesity, a surgical procedure and a treatment method using a high density laser are used, and a technology for treating obesity using cooling is also used.

A technology for treating obesity using cooling in the related art is disclosed in Korean Patent No. 10-1039758 entitled "CRYOPROTECTANT FOR USE WITH A TREATMENT DEVICE FOR IMPROVED COOLING OF SUBCUTANEOUS LIPID-RICH CELLS" and Korean Patent No. 10-1248799 entitled "CRYOPROTECTANT FOR USE WITH A TREATMENT DEVICE FOR IMPROVED COOLING OF SUBCUTANEOUS LIPID-RICH CELLS".

However, in the registered patent documents described above, as shown in FIG. 1, a coupling device or an absorption pad to provide an anti-freezing agent between a part to be treated and a heat exchange factor is required, and thus treatment expense is increased due to the increased number of parts. Further, when sucked, the gel-type anti-freezing agent is gathered at the part to be treated, and the periphery of the absorption pad is dried, thereby decreasing a suction force. Referring to FIG. 1, the coupling device 20 is located between the part to be treated 10 and the heat exchange factor 30. Further, in the coupling device 20, a middle portion made of a net or a foam material is provided between a bottom surface portion 23 having a hole 23a and a top surface portion 21, and thus, the anti-freezing agent is introduced from a supply device 25 via a pipe 24.

Furthermore, in a device for treating obesity using cooling according to the related art, a handpiece for sucking and cooling the part to be treated is used, and a suction cup 40 for sucking the part to be treated of a patient is mounted on the handpiece. According to the related art, as shown in FIG. 2, metallic cooling plates 52 of the suction cup 40 are exposed to a suction space 42, thereby making direct contact with the part to be treated 10. Thus, the anti-freezing agent or the coupling device is necessarily required. Further, according to the related art, since the amount of a patient's sucked skin is determined depending on the size of the suction cup 40, various sized suction cups are prepared, and the suction cups are replaced depending on the extent of obesity of a patient, which is inconvenient. Referring to FIG. 2, the suction cup 40 according to the related art has holes on opposite sides thereof, and a pair of cooling devices 50 including the metallic cooling plates 52, the thermoelectric element 54, and a cooler 56 are mounted on the holes, respectively. Thus, the metallic cooling plates 52 make direct contact with the part to be treated 10.

DISCLOSURE

Technical Problem

Accordingly, the present invention has been made keeping in mind the above problems occurring in the prior art, and an object of the present invention is to provide a device for treating obesity using low-cost cooling, the device being capable of treating obesity by spreading an anti-freezing agent to a part to be treated without use of an absorption pad or a coupling device accommodating the anti-freezing agent, but by surrounding the part with a film to protect the skin, and cooling only a fat portion.

Another object of the present invention is to provide a device for treating obesity using low-cost cooling, the device in which metallic cooling plates are provided on a suction cup in an in-molded manner and having a suction space may be controlled depending on the extent of obesity of a patient without replacement of the suction cup by adding a spacer mounted or demounted on the suction cup.

Technical Solution

In order to accomplish the above object, the present invention provides a device for treating obesity using cooling, including: a controller body for setting a cooling temperature and operating time, supplying cooling water for cooling a thermoelectric element, and providing suction force through a vacuum pump; a handpiece body for displaying operating conditions and providing suction force through a suction hole; a cable for connecting the controller body and the handpiece body; a suction cup mounted on the handpiece body to form a suction space; and cooling devices positioned on opposite sides of the suction cup to cool a part to be treated, which has been sucked into the suction space.

The device may further include a film for sealing an anti-freezing agent applied to the part to be treated to facilitate penetration of the anti-freezing agent into the part to be treated and to prevent the suction cup from being smeared with the anti-freezing agent, and the film may be made of one of linear low-density polyethylene (LLD-PE) and vinyl.

The handpiece body may include: a body top as an upper case; a light emitting diode (LED) assembly for displaying power supply conditions; a liquid crystal display (LCD) assembly for displaying the operating conditions; a body bottom having a suction hole and being coupled to the body top to form a space for accommodating parts therein; and a suction cup guide for guiding the suction cup.

The cable may include: a water supply pipe for supplying cooling water from the controller body to the handpiece body; a water return pipe for returning used cooling water to the controller body; a suction pipe for transmitting the suction force from the vacuum pump; an electric wire for supplying power to the thermoelectric element; and a signal wire for transmitting a temperature sensing signal.

Each of the cooling devices may include: a temperature sensor for sensing a temperature; the thermoelectric element for cooling the suction cup when power is supplied; and a cooling block for cooling heat generated from the thermoelectric element in a water cooling manner.

The suction cup may include: a cup body made of a silicone material and configured such that a bottom surface of the cup body may be fitted into the handpiece body and a first surface of the cup body making contact with the part to be treated is open to form the suction space for sucking the part to be treated inside the cup body; and cooling plates in-molded on opposite sides of the cup body, in which the cooling plates may make contact with the part to be treated via a thin silicone layer instead of making direct contact with the part to be treated so that the device may efficiently destroy fat using a small amount of anti-freezing agent while protecting a skin, and remove any gap through which air flows in, thereby increasing suction force.

The suction cup may further include: a spacer for controlling the suction space, and the spacer may include: a bottom plate; a top plate to which a support column, having coupling grooves formed at predetermined intervals, is attached; and a coupling member for varying a distance between the bottom plate and the top plate by adjusting a coupled location at the coupling grooves, in which the spacer may control the suction space of the suction cup.

The controller body may connect a left handpiece and a right handpiece, set cooling temperatures of the left and right handpieces stepwisely between <2° C. and −10° C. using a touch screen, and set an operating mode as one of a massage mode, a cooling mode, and a suction mode.

Advantageous Effects

As described above, the present invention is advantageous in that metallic cooling plates are in-molded in a suction cup made of a silicone material, in which the metallic cooling plates make contact with a part to be treated via a thin silicone layer instead of making direct contact with the part to be treated so that the device efficiently destroys fat using a small amount of anti-freezing agent while protecting a skin, and removes any gap through which air flows in, thereby increasing suction force.

Furthermore, the present invention is advantageous in that the anti-freezing agent is applied to the part to be treated, and the anti-freezing agent is sealed with a film to facilitate penetration of the anti-freezing agent into the part to be treated and to prevent the suction cup from being smeared with the anti-freezing agent. Thus, use of a liner or an absorption pad and a coupling device is not required, thereby reducing cost and easily controlling a handpiece.

Further, the present invention is advantageous in that a suction space may be easily controlled depending on the extent of obesity without replacement of the suction cup by mounting or demounting a spacer on the suction cup of the hand piece.

MODE FOR INVENTION

Technical problems solved by the present invention and implementation of the present invention will be further clarified by preferred embodiments of the present invention described below. The embodiments of the present invention are exemplified merely for the purpose of illustrating the present invention, and the present invention should not be limited thereto.

Figure 1:
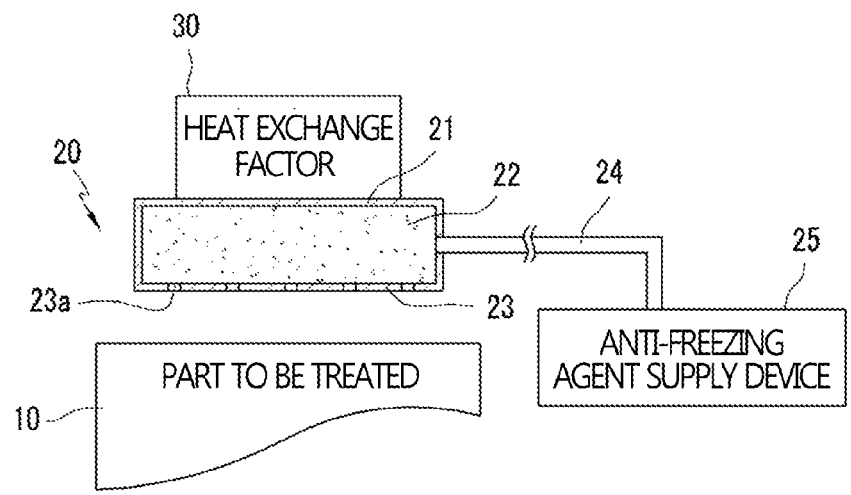
FIG. 1 is a view of an example of a coupling device of a device for treating obesity using cooling according to the related art.
Figure 2:
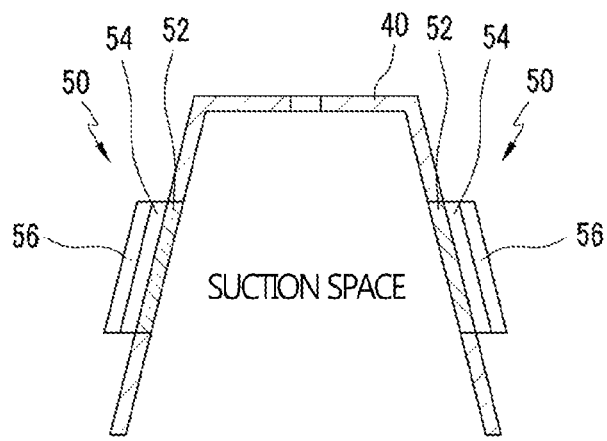
FIG. 2 is a view of an example of a suction cup of the device for treating obesity using cooling according to the related art.
Figure 3:
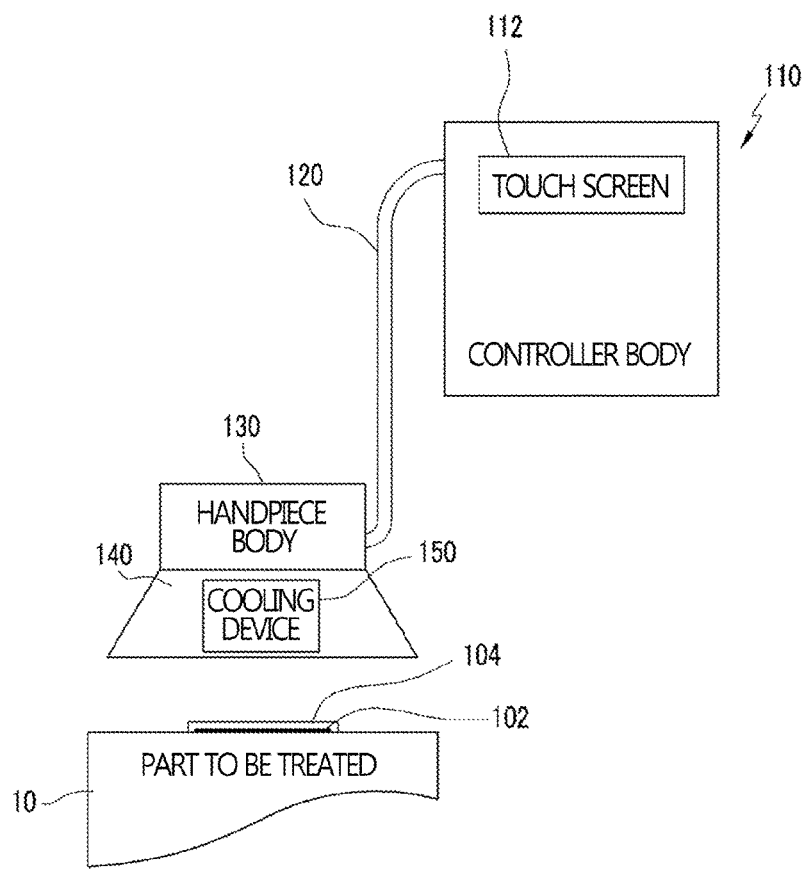
FIG. 3 is a schematic view of a device for treating obesity using cooling according to the present invention.

FIG. 3 is a schematic view of a device for treating obesity using cooling according to the present invention.

The device for treating obesity using cooling according to the present invention, as shown in FIG. 3, includes a controller body 110 for setting a cooling temperature and operating time via a touch screen 112, supplying cooling water for cooling heat generated from a thermoelectric element, and providing suction force; a cable 120 for connecting the controller body 110 and a handpiece body 130; the handpiece body 130 for displaying operating conditions and providing suction force through a suction hole; a suction cup 140 mounted on the handpiece body 130 to form a suction space; and cooling devices 150 positioned on opposite sides of the suction cup 140 to cool a part to be treated, which has been sucked into the suction space. Although the controller body 110 is connected to one handpiece in an embodiment according to the present invention, the controller body may be connected to a plurality of handpieces, such as left and a right handpieces.

Referring to FIG. 3, the anti-freezing agent 102 is applied to the part to be treated 10, and the anti-freezing agent 102 is sealed with a film 104 to facilitate penetration of the anti-freezing agent 102 into the part to be treated 10 and to prevent the suction cup 140 from being smeared with the anti-freezing agent 102. In this case, the film 104 may be made of one of linear low-density polyethylene (LLD-PE), rubber, and vinyl. Further, the vinyl film may be provided with a Velcro tape for sealing. Furthermore, as the anti-freezing freezing agent 102 for protecting a skin, a gel-type composition including propylene glycol (for example, 20% by weight or more) may be used.

The controller body 110 with casters may be moved using a handle, and includes: a radiator for supply cooling water, and returning used cooling water; a vacuum pump for providing suction force; and a touch screen 112 for displaying the operating conditions and inputting manipulation.

The cable 120 includes a water supply pipe 121 (shown in FIG. 4) for supplying water from the controller body 110 to the handpiece body 130, a water return pipe 122 (shown in FIG. 4) for returning used water to the controller body 110, and a suction pipe 123 (shown in FIG. 4) for transmitting the suction force from the vacuum pump. Further, the cable 120 also includes an electric wire for supplying power to the handpiece body 130 and the thermoelectric element, and a signal wire (omitted in the drawings) for transmitting a temperature sensing signal.

The suction cup 140 includes a cup body 142 made of a silicone material, and metallic cooling plates 144 in-molded on opposite sides of the cup body 142. Further, a bottom surface of the cup body 142 is fitted into the handpiece body 130, and a first surface of the cup body 142 making contact with the part to be treated 10 is open. Thus, the suction space 148 (shown in FIG. 5) for sucking the part to be treated 10 inside the cup body 142 is formed. The suction space 148 may be controlled by using the spacer 160, which will be described later. Furthermore, the metallic cooling plates 144, which are in-molded in the cup body 142 made of a silicone material, are provided on the opposite sides of the suction cup 140 according to the present invention, thereby preventing the metallic cooling plates 144 from making direct contact with the part to be treated 10. Further, cooling devices 150 are mounted on the metallic cooling plates 144.

Figure 4:
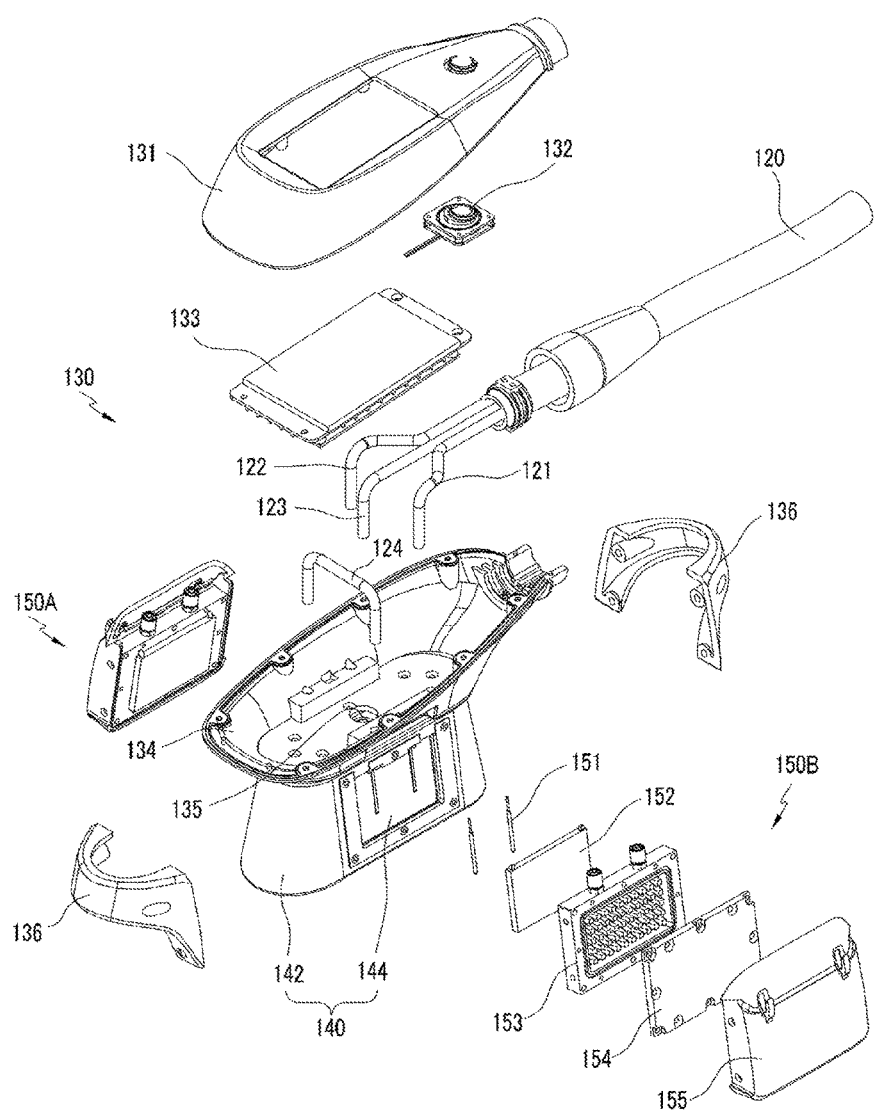
FIG. 4 is an exploded perspective view of a handpiece of the device for treating obesity using cooling according to the present invention.

FIG. 4 is an exploded perspective view of the handpiece of the device for treating obesity using cooling according to the present invention.

The handpiece of the device for treating obesity using cooling according to the present invention includes: the handpiece body 130; the suction cup 140; and a pair of cooling devices 150A and 150B. The handpiece body 130, as shown in FIG. 4, includes: a body top 131 as an upper case; a light emitting diode (LED) assembly 132 for displaying power supply conditions; a liquid crystal display (LCD) assembly 133 for displaying the operating conditions; a body bottom 134 having the suction hole 135 and being coupled to the body top 131 to form a space for accommodating parts therein; and a suction cup guide 136 for guiding the suction cup.

The cooling devices 150A and 150B, as shown in FIG. 4, include: a temperature sensor 151 for sensing a temperature; the thermoelectric element 152; a cooling block 153; a cooling block top 154; and a cooling block cover 155. In this case, when power is applied to the thermoelectric element 152, the cooling devices 150A and 150B cool the cooling plates 144, and the cooling block 153 cools the generated heat in a water cooling manner. A pipe 124 provided inside the handpiece body 130 may flow the cooling water between the cooling devices 150A and 150B on the opposite sides of the suction cup.

Figure 5:
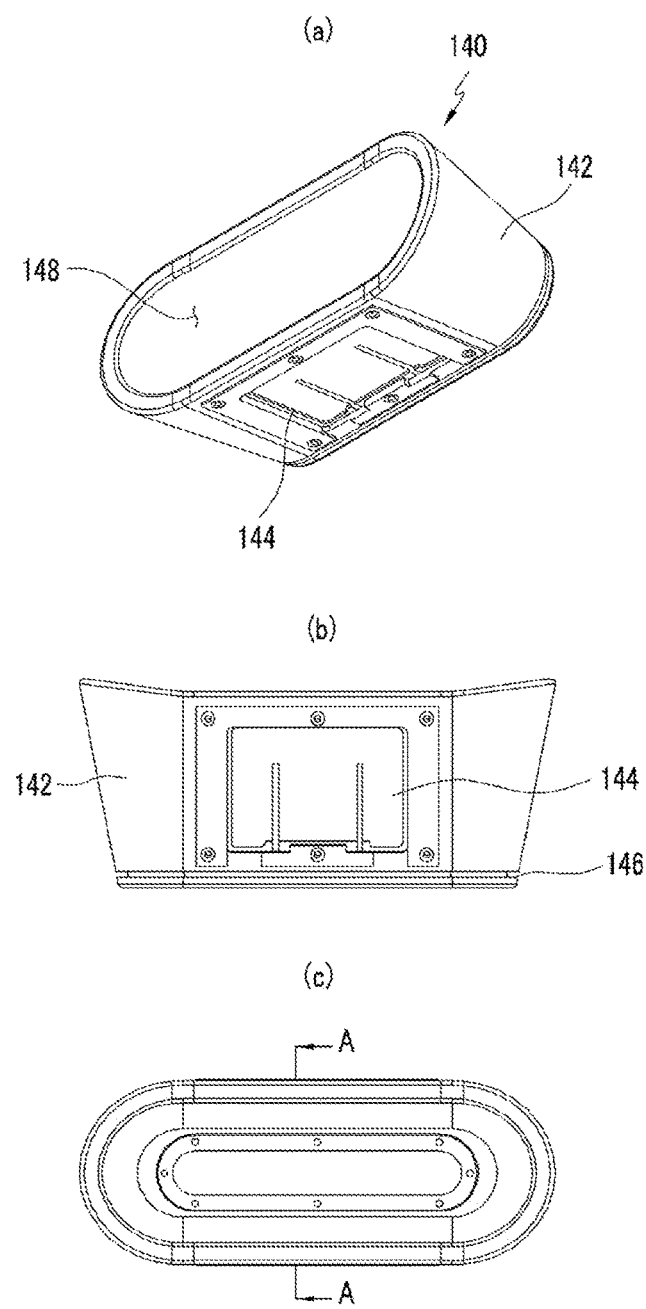
FIG. 5 is a view of a suction cup of the handpiece of the device for treating obesity using cooling according to the present invention.

FIG. 5 is a view of the suction cup of the handpiece of the device for treating obesity using cooling according to the present invention, and FIG. 5(*a*) is a perspective view, FIG. 5(*b*) is a lateral view, and FIG. 5(*c*) is a plane view. Further, FIG. 6 is a cross-sectional view taken along line A-A of the suction cup shown in FIG. 5(*c*).

Figure 6:
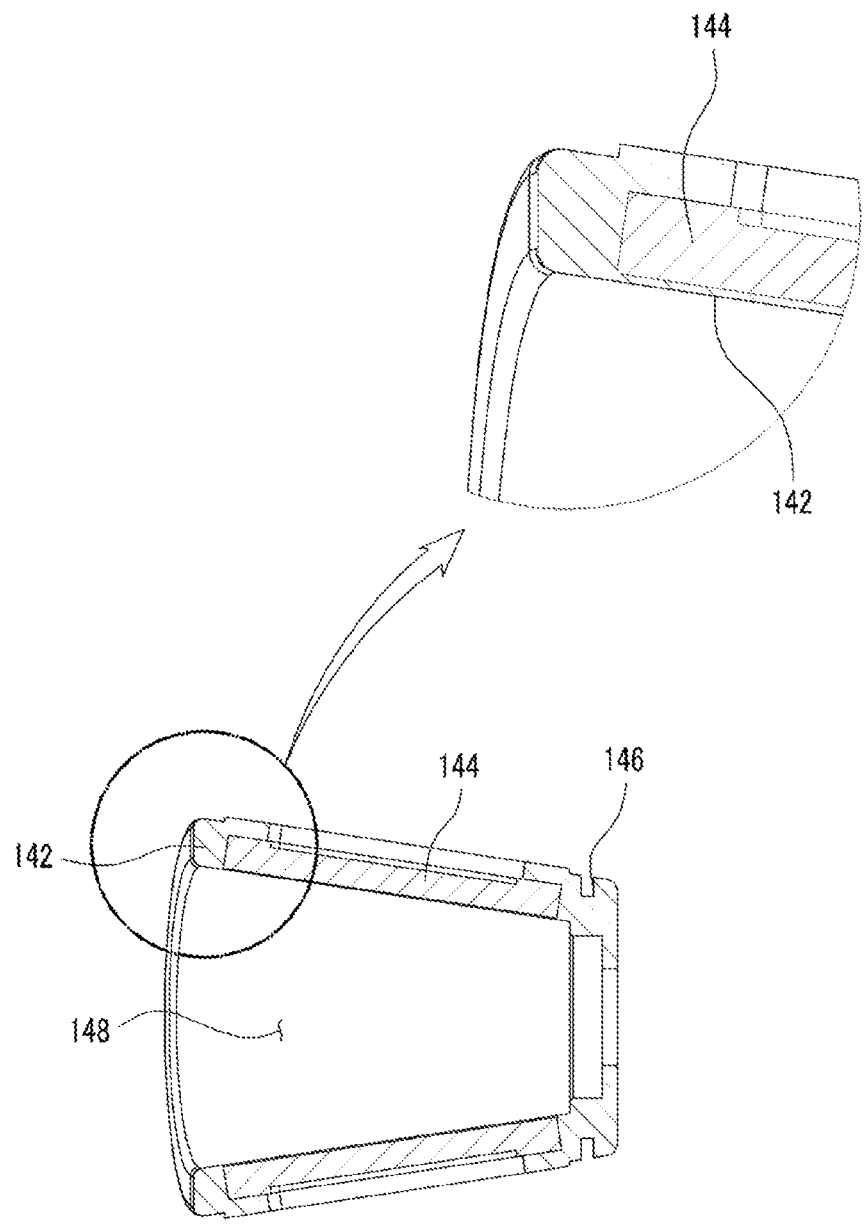
FIG. 6 is a cross-sectional view taken along line A-A of the suction cup shown in FIG. 5.

The suction cup 140, as shown in FIGS. 5 and 6, includes: the cup body 142 made of a silicone material; and the metallic cooling plates 144 in-molded on the opposite sides of the cup body 142, respectively. Further, a groove 146 for being fitted into the body bottom 134 of the handpiece body 130 is formed in the bottom surface of the cup body 142, and the suction space 148 for sucking the part to be treated 10 inside the cup body is formed by coupling the body bottom 134 to the cup body 142.

Referring to FIGS. 5 and 6, in the suction cup 140 according to the present invention, the metallic cooling plates 144 are in-molded in the cup body 142, and the metallic cooling plates 144 and the cup body 142 are integrally formed, thereby preventing the suction force from decreasing. In this case, since a silicone layer of the cup body 142 is provided between the metallic cooling plates 144 and the part to be treated 10 sucked in the suction space 148, the metallic cooling plates 144 are prevented from making direct contact with the part to be treated 10. Thus, low temperature energy is transferred and a freezing phenomenon is decreased. Accordingly, the anti-freezing agent is not required, or the small amount of the anti-freezing agent is sufficient, thereby providing an advantage in that an absorption pad or a coupling device is not required.

Figure 7:
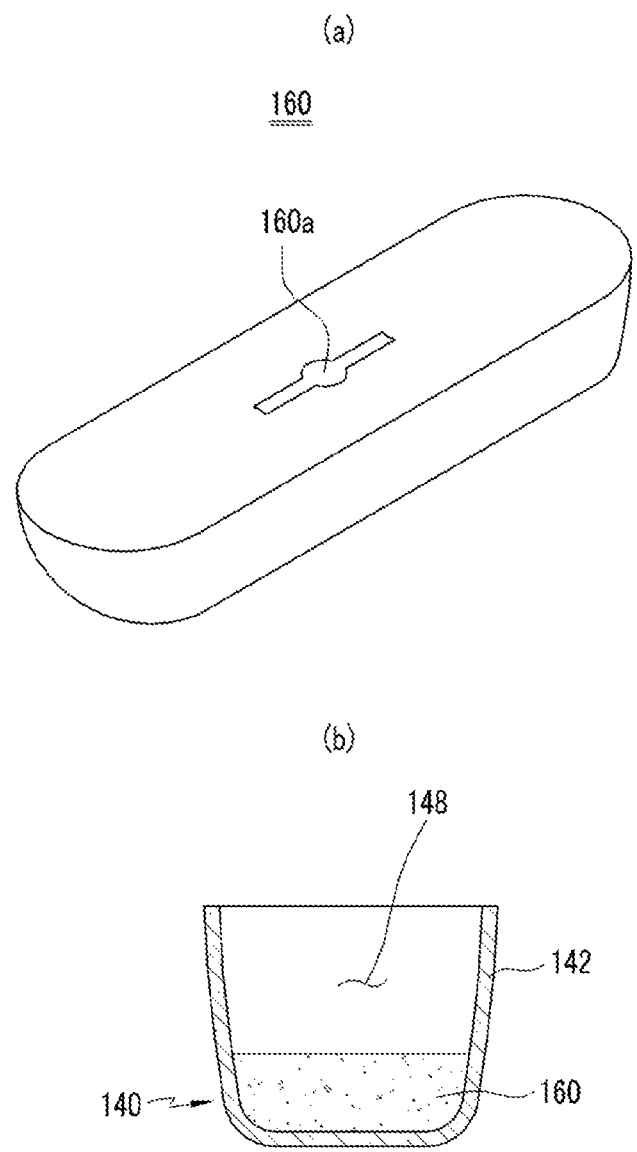
FIG. 7 is a first embodiment of a spacer mounted or demounted on the suction cup of the handpiece according to the present invention.

FIG. 7 is a first embodiment of the spacer mounted or demounted on the suction cup of the handpiece according to the present invention. Further, FIG. 7(*a*) is a perspective view of a fixed sized spacer 160, and FIG. 7(*b*) is a cross-sectional view of a state of the fixed sized spacer 160 mounted on the suction cup.

As shown in FIG. 7, in the device for treating obesity using cooling according to the present invention, thickness of the bottom surface of the suction cup 140 is increased by inserting the fixed sized spacer 160 having a penetration hole 160*a* into the suction cup 140. Thus, the size of the suction space 148 is decreased, thereby reducing the part to be treated 10 sucked therein. That is, according to the related art, in case of a low rate of obesity or the small size of part to be treated, it is required to replace the suction cup with a small sized suction cup. However, according to the present invention, the size of the suction space 148 may be easily controlled by preparing various fixed sized spacers and replacing the spacer 160 without replacement of the suction cup 140.

Figure 8:
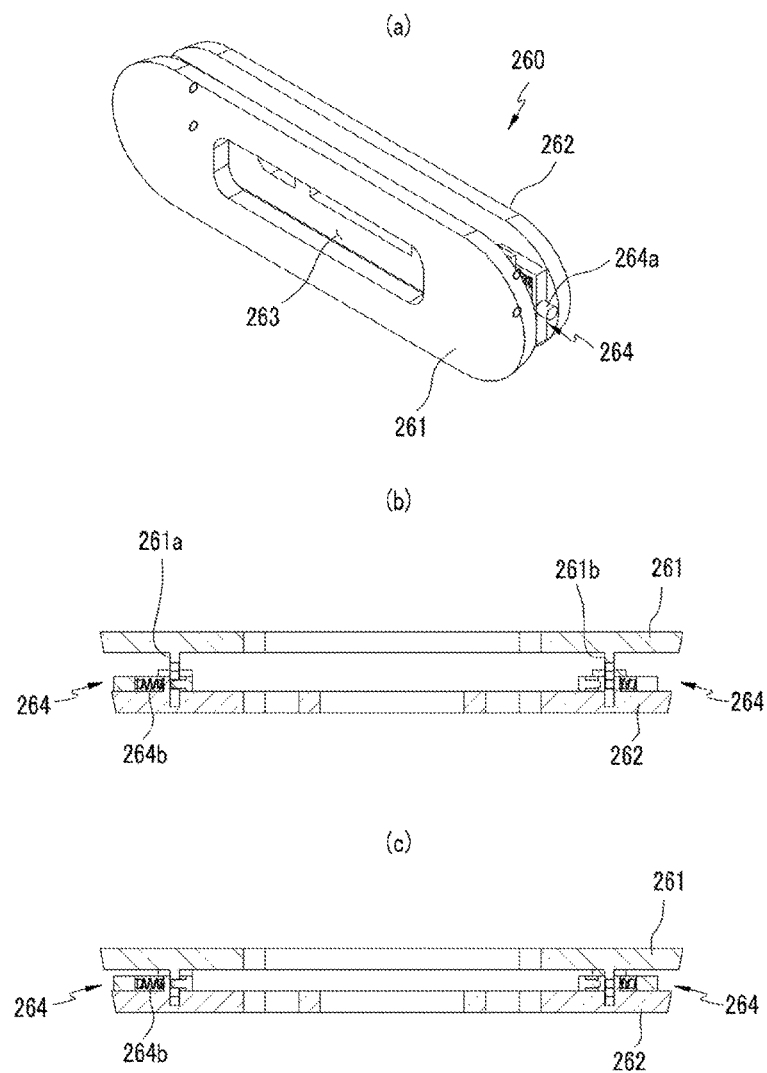
FIG. 8 is a second embodiment of the spacer mounted or demounted on the suction cup of the handpiece according to the present invention.

FIG. 8 is a second embodiment of the spacer mounted or demounted on the suction cup of the handpiece according to the present invention. Further, FIG. 8(*a*) is a perspective view of a variable sized spacer 260, FIG. 8(*b*) is a view of an extended state of the variable sized spacer 260, and FIG. 8(*c*) is a view of a shortened state of the variable sized spacer 260.

The variable sized spacer 260 according to the present invention, as shown in FIG. 8, includes: a bottom plate 262; a top plate 261 to which support columns 261*a* and 261*b*, having coupling grooves formed at predetermined intervals, are attached; and a coupling member 264 for varying a distance between the bottom plate 262 and the top plate 261 by adjusting a coupled location at the coupling grooves. Thus, the suction space of the suction cup may be controlled. Further, the penetration hole 263 is formed in the top plate 261 and the bottom plate 262, and the coupling member 264 includes a button 264*a* protruding from a first end of the coupling member 264 by a spring 264*b*. Thus, heights of the support columns 261*a* and 261*b* are controlled by pushing the button 264*a*, and after increasing or decreasing the distance between the top and bottom plates 261 and 262, the heights of the support columns 261*a* and 261*b* are fixed by releasing the button 264*a*.

Figure 9:
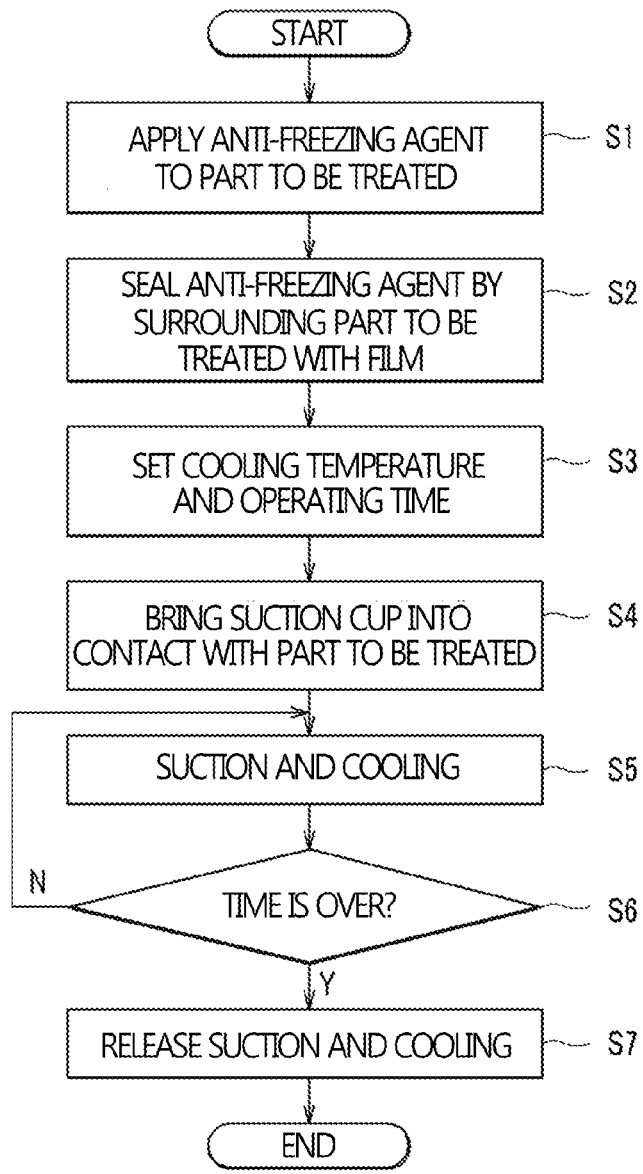
FIG. 9 is a diagram illustrating an operating procedure of the device for treating obesity using cooling according to the present invention.
Figure 10:
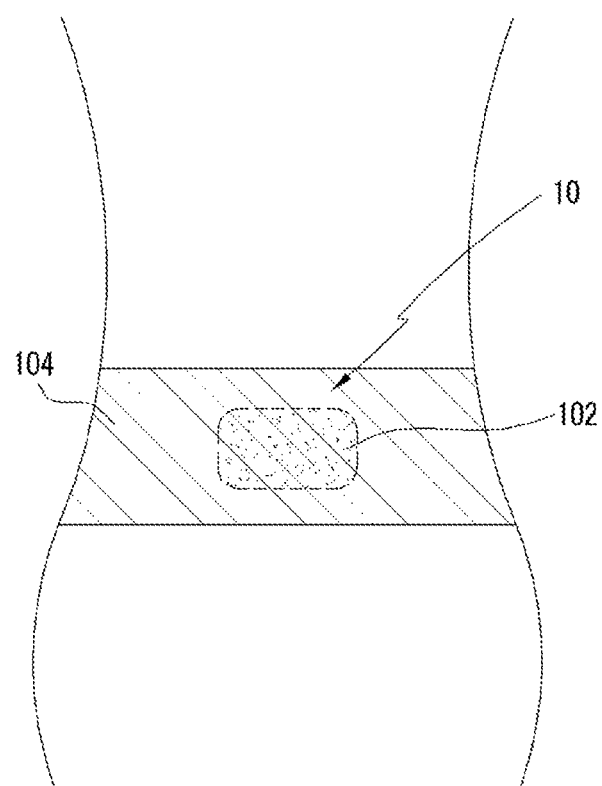
FIG. 10 is a schematic view of a state of surrounding a part to be treated with a film according to the present invention.

FIG. 9 is a diagram illustrating an operating procedure of the device for treating obesity using cooling according to the present invention. FIG. 10 is a schematic view of a state of surrounding the part to be treated with the film according to the present invention.

As shown in FIGS. in 9 and 10, in the device for treating obesity using cooling according to the present invention, when the part to be treated 10 is sucked into the suction cup 140 by the suction force by bringing the suction cup 140 of the handpiece into contact with the part to be treated 10, fat cells are destroyed in such a way that the cooling device 150 cools the part to be treated, thereby treating obesity.

Referring to FIGS. 9 and 10, the gel-type anti-freezing agent 102 is applied to the part to be treated 10 before operating the device. Further, the part to be treated 10, to which the anti-freezing agent 102 has been applied, is sealed with the film 104 to facilitate the penetration of the anti-freezing agent 102 into the part to be treated 10 and to prevent the suction cup 140 of the handpiece from being smeared with the anti-freezing agent 102 (S1 and S2).

Thereafter, after setting the cooling temperature and the operating time of the handpiece to be used via the touch screen 112 of the controller body, the suction cup makes contact with the part to be treated, and suction and cooling are performed by selecting an operating mode (S3 to S5). The cooling temperature may be set stepwise, preferably between −2° C. and −10° C. According to the embodiments of the present invention, a first stage is −3° C., a second stage is −5° C., a third stage is −7° C., and a fourth stage is −9° C. Further, a massage mode, a cooling mode, and a suction mode are provided as operating modes.

Thereafter, when the predetermined operating time is over, the suction is released and the cooling is stopped. Further, after the film 104 is removed from the part to be treated, the anti-freezing agent 102 is removed (S6 and S7).

Although an embodiment of the present invention has been described with reference to the accompanying drawings for illustrative purposes, those skilled in the art will appreciate that various modifications, additions and substitutions are possible without departing from the scope and spirit of the invention as disclosed in the accompanying claims.

DESCRIPTION OF REFERENCE CHARACTERS OF IMPORTANT PARTS

102: anti-freezing agent, 104: film
110: controller body, 112: touch screen
120: cable, 130: handpiece body
140: suction cup, 150: cooling device
160, 260: spacer

What is claimed is:

1. A device for treating obesity using cooling, comprising:
a controller body for setting a cooling temperature and operating time, supplying cooling water for cooling a thermoelectric element, and providing suction force through a vacuum pump;
a handpiece body for displaying operating conditions and providing suction force through a suction hole;
a cable for connecting the controller body and the handpiece body;
a suction cup mounted on the handpiece body to form a suction space; and
cooling devices positioned on opposite sides of the suction cup to cool a part to be treated, which has been sucked into the suction space,
wherein the suction cup comprises:
a cup body made of a silicone material and configured such that a bottom surface of the cup body is fitted into the handpiece body and a first surface of the cup body making contact with the part to be treated is open to form the suction space for sucking the part to be treated inside the cup body;
cooling plates in-molded on opposite sides of the cup body; and
a spacer for controlling the suction space,
wherein the spacer comprises:
a bottom plate;
a top plate to which a support column, having coupling grooves formed at predetermined intervals, is attached; and
a coupling member for varying a distance between the bottom plate and the top plate by adjusting a coupled location at the coupling grooves, wherein
the spacer controls the suction space of the suction cup.

2. The device as set forth in claim 1, further comprising:
a film for sealing an anti-freezing agent applied to the part to be treated to facilitate penetration of the anti-freezing agent into the part to be treated and to prevent the suction cup from being smeared with the anti-freezing agent.

3. The device as set forth in claim 2, wherein the film is made of one of linear low-density polyethylene (LLD-PE) and vinyl.

4. The device as set forth in claim 2, wherein the anti-freezing agent is a gel-type composition including propylene glycol.

5. The device as set forth in claim 1, wherein the handpiece body comprises:
a body top as an upper case;
a light emitting diode (LED) assembly for displaying power supply conditions;
a liquid crystal display (LCD) assembly for displaying the operating conditions; and
a body bottom having a suction hole and being coupled to the body top to form a space for accommodating parts therein.

6. The device as set forth in claim 1, wherein the cable comprises:
a water supply pipe for supplying cooling water from the controller body to the handpiece body;
a water return pipe for returning used cooling water to the controller body;
a suction pipe for transmitting the suction force from the vacuum pump;
an electric wire for supplying power to the thermoelectric element; and
a signal wire for transmitting a temperature sensing signal.

7. The device as set forth in claim 1, wherein each of the cooling devices comprises:
a temperature sensor for sensing a temperature;
the thermoelectric element for cooling the suction cup when power is supplied; and
a cooling block for cooling heat generated from the thermoelectric element in a water cooling manner.

8. The device as set forth in claim 1,
wherein
the cooling plates are configured to contact with the part to be treated via a thin silicone layer instead of making direct contact with the part to be treated so that the device efficiently destroys fat using a small amount of anti-freezing agent while protecting a skin, and removes any gap through which air flows in, thereby increasing suction force.

9. The device as set forth in claim 1, wherein the controller body connects a left handpiece and a right handpiece, sets cooling temperatures of the left and right handpieces stepwisely between −2° C. and −10° C. using a touch screen, and sets an operating mode.

* * * * *